United States Patent [19]

Linguenheld et al.

[11] Patent Number: 4,504,682
[45] Date of Patent: Mar. 12, 1985

[54] NOVEL POLYOXAALKYL AMINOALCOHOLS

[75] Inventors: Louis Linguenheld, Ruelisheim; Gerard Soula, Meyzieu, both of France

[73] Assignee: Rhone-Poulenc Industries, Paris, France

[21] Appl. No.: 455,898

[22] Filed: Jan. 5, 1983

Related U.S. Application Data

[62] Division of Ser. No. 296,214, Aug. 25, 1981, Pat. No. 4,429,160.

[30] Foreign Application Priority Data

Aug. 27, 1980 [FR] France ................................ 80 18561

[51] Int. Cl.³ .............................................. C07C 85/06
[52] U.S. Cl. ..................................................... 564/480
[58] Field of Search ......................................... 564/480

[56] References Cited

U.S. PATENT DOCUMENTS

| | | | |
|---|---|---|---|
| 2,529,923 | 11/1950 | Dickey et al. | 564/480 |
| 2,928,877 | 3/1960 | Jaul et al. | 564/480 |
| 3,352,916 | 11/1967 | Zech | 564/480 X |
| 3,714,259 | 1/1973 | Lichtenwacter et al. | 564/480 |
| 3,847,992 | 11/1974 | Moss | 564/480 X |
| 3,957,875 | 5/1976 | Ferrell et al. | 564/480 |
| 4,151,204 | 4/1979 | Ichikawa et al. | 564/480 |

Primary Examiner—Paul F. Shaver
Attorney, Agent, or Firm—Burns, Doane, Swecker & Mathis

[57] ABSTRACT

Novel polyoxaalkyl aminoalcohols, well adapted for the complexation/solubilization of a wide variety of cations, have the structural formula:

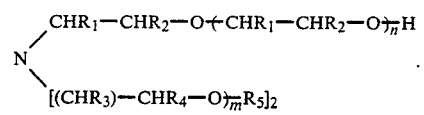

6 Claims, No Drawings

NOVEL POLYOXAALKYL AMINOALCOHOLS

This application is a division of application Ser. No. 296,214, filed Aug. 25, 1981, now U.S. Pat. No. 4,429,160, issued Jan. 31, 1984.

BACKGROUND OF THE INVENTION

1. Field of the Invention

The present invention relates to novel polyoxaalkyl aminoalcohols, a process for the preparation thereof, and the complexation of cations therewith.

2. Description of the Prior Art

Certain polyoxaalkyl aminoalcohols are known to this art. Compare British Patent Specification No. 897,163 which relates to those aminoalcohols having the structural formula:

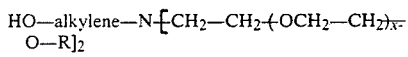

wherein R is an alkyl radical having from 1 to 6 carbon atoms, and x is an integer ranging from 2 to 10.

These aminoalcohols may be prepared by reacting an alkanolamine, $HO$-alkylene-$NH_2$, with, for example, an alkoxypolyethylene-oxyethyl chloride having the structural formula:

Compare also published German Patent Application No. 2,835,984, and published European Patent Application No. 5,094.

SUMMARY OF THE INVENTION

Accordingly, a major object of the present invention is the provision of novel and different aminoalcohols, said novel compounds being polyoxyalkyl aminoalcohols having the structural formula:

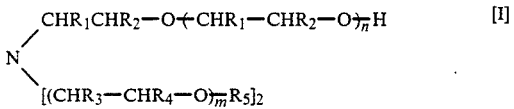

wherein $R_1$, $R_2$, $R_3$ and $R_4$, which may be identical or different, are each a hydrogen atom or an alkyl radical having from 1 to 4 carbon atoms; $R_5$ is an alkyl, or phenyl substituted alkyl radical having from 1 to 12 carbon atoms, a cycloalkyl radical having from 3 to 12 carbon atoms, a phenyl, or alkyl substituted phenyl radical with said alkyl substituent having from 1 to 12 carbon atoms; n is an integer ranging from 1 to 9; and m is an integer ranging from 1 to 10.

DETAILED DESCRIPTION OF THE INVENTION

More particularly according to this invention, preferred polyoxaalkyl aminoalcohols of the formula [I] are those in which $R_1$, $R_2$, $R_3$ and $R_4$ are either identical or different and are either hydrogen or methyl; $R_5$ is an alkyl radical having from 1 to 6 carbons, more preferably 1 to 4 carbon atoms, a cyclohexyl radical, a phenyl radical or a $C_1$-$C_4$ alkyl substituted phenyl radical; n is an integer ranging from 1 to 5, more preferably ranging from 1 to 3; and m is an integer ranging from 1 to 6, more preferably ranging from 1 to 4.

Exemplary of the novel polyoxaalkyl aminoalcohols according to the invention are:

[1] N-(5'-Hydroxy-3'-oxapentyl)-5-aza-2,8-dioxanonane;

[2] N-(5'-Hydroxy-3'-oxapentyl)-6-aza-3,9-dioxanonane;

[3] -N(5'-Hydroxy-3'-oxapentyl)-7-aza-4,10-dioxatridecane;

[4] N-(5'-Hydroxy-3'-oxapentyl)-8-aza-5,11-dioxapentadecane;

[5] N-(5'-Hydroxy-3'-oxapentyl)-8-aza-2,5,11,14-tetraoxapentadecane;

[6] N-(5'-Hydroxy-3'-oxapentyl)-9-aza-3,6,12,15-tetraoxaheptadecane;

[7] N-(5'-Hydroxy-3'-oxapentyl)-10-aza-4,7,13,16-tetraoxanonadecane;

[8] N-(5'-Hydroxy-3'-oxapentyl)-11-aza-5,8,14,17-tetraoxaheneicosane;

[9] N-(5'-Hydroxy-3'-oxapentyl)-12-aza-3,6,9,15,18,21-hexaoxatricosane;

[10] N-(5'-Hydroxy-3'-oxapentyl)-13-aza-4,7,10,16,19,22-hexaoxapentacosane;

[11] N-(5'-Hydroxy-3'-oxapentyl)-14-aza-5,8,11,17,20,23-hexaoxaheptacosane;

[12] Those aminoalcohols having the structural formula:

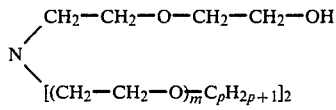

wherein m ranges from 1 to 3, and p ranges from 1 to 4;

[13] N-(8'-Hydroxy-3',6'-dioxaoctyl)-5-aza-2,8-dioxanonane;

[14] N-(8'-Hydroxy-3',6'-dioxaoctyl)-6-aza-3,9-dioxaundecane;

[15] N-(8'-Hydroxy-3',6'-dioxaoctyl)-7-aza-4,10-dioxatridecane;

[16] N-(8'-Hydroxy-3',6'-dioxaoctyl)-8-aza-5,11-dioxapentadecane;

[17] N-(8'-Hydroxy-3',6'-dioxaoctyl)-8-aza-2,5,11,14-tetraoxapentadecane;

[18] N-(8'-Hydroxy-3',6'-dioxaoctyl)-9-aza-3,6,12,15-tetraoxaheptadecane;

[19] N-(8'-Hydroxy-3',6'-dioxaoctyl)-10-aza-4,7,13,16-tetraoxanonadecane;

[20] N-(8'-Hydroxy-3',6'-dioxaoctyl)-11-aza-5,8,14,17-tetraoxaheneicosane;

[21] N-(8'-Hydroxy-3',6'-dioxaoctyl)-11-aza-2,5,8,14,17,20-hexaoxaheneicosane;

[22] N-(8'-Hydroxy-3',6'-dioxaoctyl)-12-aza-3,6,9,15,18,21-hexaoxatricosane;

[23] N-(8'-Hydroxy-3',6'-dioxaoctyl)-13-aza-4,7,10,16,19,22-hexaoxapentacosane;

[24] N-(8'-Hydroxy-3',6' -dioxaoctyl)-14-aza-5,8,11,17,20,23-hexaoxaheptacosane;

[25] Those aminoalcohols having the structural formula:

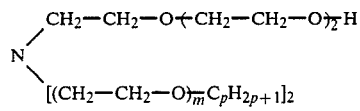

wherein m ranges from 1 to 3, and p ranges from 1 to 4;

[26] N-(11'-Hydroxy-3',6',9'-trioxaundecyl)-5-aza-2,8-dioxanonane;
[27] N-(11'-Hydroxy-3',6',9'-trioxaundecyl)-6-aza-3,9-dioxaundecane;
[28] N-(11'-Hydroxy-3',6',9,'trioxaundecyl)-7-aza-4,10-dioxatridecane;
[29] N-(11'-Hydroxy-3',6',9'-trioxaundecyl)-8-aza-5,11-dioxapentadecane;
[30] N-(11'-Hydroxy-3',6',9'-trioxaundecyl)-8-aza-2,5,11,14-tetraoxapentadecane;
[31] N-(11'-Hydroxy-3',6',9'-trioxaundecyl)-9-aza-3,6,12,15-tetraoxaheptadecane;
[32] N-(11'-Hydroxy-3',6',9'-trioxaundecyl)-10-aza-4,7,13,16-tetraoxanonadecane;
[33] N-(11'-Hydroxy-'3',6',9'-trioxaundecyl)-11-aza-5,8,14,17-tetraoxaheneicosane;
[34] N-(11'-Hydroxy-3',6',9'-trioxaundecyl)-11-aza-2,5,8,14,17,20-hexaoxaheneicosane;
[35] N-(11'-Hydroxy-3',6',9'-trioxaundecyl)-12-aza-3,6,9,15,18,21-hexaoxatricosane;
[36] N-(11'-Hydroxy-3',6',9'-trioxaundecyl)-13-aza-4,7,10,16,19,22-hexaoxapentacosane;
[37] N-(11'Hydroxy-3',60',9'-trioxaundecyl)-14-aza-5,8,11,17,20,23-hexaoxaheptacosane;
[38] Those aminoalcohols having the structural formula:

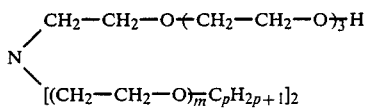

wherein m ranges from 1 to 3, and p ranges from 1 to 4; and
[39] Those aminoalcohols having the structural formula:

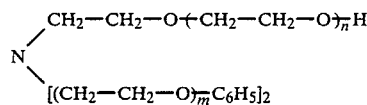

wherein n ranges from 1 to 3, and m also ranges from 1 to 3.

The present invention also relates to a process for the preparation of the polyoxaalkyl aminoalcohols having the structural formula [I].

Such process is characterized by reacting a polyalkylene glycol having the structural formula:

$$HO-CHR_1-CHR_2\text{-}(O-CHR_1-CHR_2-O)_{\overline{n}}H \quad [II]$$

wherein $R_3$, $R_4$, $R_5$ and n are as defined above, with a bis(polyoxaalkyl)amine having the structural formula:

$$HN\text{-}[(CHR_3-CHR_4-O)_{\overline{m}}R_5]_2 \quad [III]$$

wherein $R_3$, $R_4$, $R_5$ and m are also as defined above, in a molar ratio of the polyalkylene glycol of formula [II] to the bis(polyoxaalkyl)amine of formula [III] of at least 1.5 times in excess of the stoichiometric amount required for preparation of the polyoxaalkyl aminoalcohols [I], at a temperature ranging from 120° to 220° C., preferably ranging from 150° to 200° C., and in the presence of a catalytically effective amount of a hydrogenation/dehydrogenation catalyst. The desired polyoxaalkyl aminoalcohol of formula [I] is thence conveniently separated from the mixture of reaction.

In a preferred embodiment according to the invention, a nickel catalyst is utilized, preferably of Raney nickel or Harshaw nickel type; the amount of catalyst advantageously ranges from 1 to 15% by weight of the amount of the bis(polyoxaalkyl)amine reactant [III], and preferably from 2 to 6% by weight thereof.

The molar ratio of the polyalkylene glycol [II] to the bis(polyoxaalkyl)amine [III] advantageously ranges from 1.5 to 10 times the stoichiometric amount thereof, and preferably from 2 to 6 times said stoichiometric amount.

The process according to the invention is advantageously carried out under a hydrogen atmosphere, or blanket, at a pressure of less than 20 bars, preferably at atmospheric pressure, and under vigorous agitation until the polyalkylene glycol has disappeared. The reaction characteristically takes from 2 to 10 hours for completion, typically from 3 to 4 hours. The amount of hydrogen advantageously utilized is on the order of 1 to 10% by weight of the polyalkylene glycol [II] and preferably is on the order of 1 to 5% by weight thereof.

The water formed during the course of the subject reaction may conveniently be eliminated from the reaction medium by means of a gaseous sweep, such as hydrogen, when employed, or nitrogen.

Exemplary of the polyalkylene glycol reactants [II] according to the invention are:
[1] Diethylene glycol;
[2] Triethylene glycol; and
[3] Tetraethylene glycol.

And exemplary of the bis(polyoxaalkyl)amine reactants [III] are:
[1] 5-Aza-2,8-dioxanonane;
[2] 6-Aza-3,9-dioxaundecane;
[3] 7-Aza-4,10-dioxatridecane;
[4] 8-Aza-5,11-dioxapentadecane;
[5] 8-Aza-2,5,11,14-tetraoxapentadecane;
[6] 9-Aza-3,6,12,15-tetraoxaheptadecane;
[7] 10-Aza-4,7,13,16-tetraoxanonadecane;
[8] 11-Aza-5,8,14,17-tetraoxaheneicosane;
[9] 11-Aza-2,5,8,14,17,20-hexaoxaheneicosane;
[10] 12-Aza-3,6,9,15,18,21-hexaoxatricosane;
[11] 13-Aza-4,7,10,16,19,22-hexaoxapentacosane;
[12] 14-Aza-5,8,11,17,20,23-hexaoxaheptacosane;
[13] Those bis(polyoxaalkyl)amines having the structural formula:

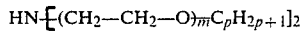

wherein m ranges from 1 to 3, and p ranges from 1 to 4; and
[14] Those bis(polyoxaalkyl)amines having the structural formula:

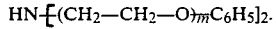

Also consistent with the present invention, the subject polyoxaalkyl aminoalcohols are admirably well suited as cation complexing agents.

Representative of the cations conveniently complexed by the polyoxaalkyl aminoalcohols according to the invention are: $NH_4^+$ and the cations of metals of the Groups IA to VIIA, VIII and IB to VB of the Periodic Table, and preferably the alkali or alkaline earth metal cations, e.g., Na, K, Li, Cs, Ca and Ba.

Moreover, complexation of the inorganic or organic salts of the immediately aforesaid metals, including the ammonium salts, with the subject polyoxaalkyl aminoalcohols gives rise to the solubilization of such salts, or markedly enhances the solubility of such salts in organic solvents, in which solvents or media said salts are typically insoluble, or only slightly soluble.

In order to further illustrate the present invention and the advantages thereof, the following specific examples are given, it being understood that same are intended only as illustrative and in nowise limitative.

EXAMPLE 1

Preparation of N-(5'-hydroxy-3'-oxapentyl)-9-aza-3,6,12,15-tetraoxaheptadecane having the structural formula

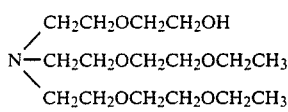

Into a three-necked, 2 liter flask, equipped with means for agitation, a hydrogen inlet, a column and a condenser for the recovery of water, the following ingredients were charged:

| (i) | Diethylene glycol | 1076 g (10.6 moles) |
|---|---|---|
| (ii) | Raney Ni, dehydrated | 125 g |
| (iii) | 9-Aza-3,6,12,15-tetraoxaheptadecane | 498 g (2 moles) |

The mixture was agitated under a stream of hydrogen (1 liter/min) and heated for 3 hours at 170° C. 106 g Water and the light products corresponding to the dehydration products of diethylene glycol were collected. After cooling and separation of the Raney nickel, the mixture was subjected to distillation to recover 888 g diethylene glycol and 380 g of the desired product, which boiled at Bp$_1$: 193° C.

The yield obtained was 55% with respect to the secondary amine reactant.

EXAMPLE 2

Preparation of N-(8'-hydroxy-3',6'-dioxaoctyl)-9-aza-3,6,12,15-tetraoxoheptadecane having the structural formula

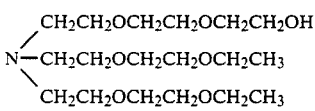

Following the same procedure and utilizing the same apparatus as in Example 1, the following ingredients were reacted:

| (i) | Triethylene glycol | 890 g (6 moles) |
|---|---|---|
| (ii) | Raney nickel, dehydrated | 160 g |
| (iii) | 9-Aza-3,4,12,15-tetraheptadecane | 498 g (2 moles) |

After 3 hours of heating at 180° C. and the subsequent filtration of the Raney nickel therefrom, the mixture was subjected to distillation to eliminate the triethylene glycol. 610 g of the expected product were recovered, in the form of a brown molten liquid having a purity of 88.1%.

The yield obtained with respect to the secondary amine reactant was 71%.

EXAMPLE 3

Preparation of N-(8'-hydroxy-3',6'-dioxaoctyl)-11-aza-2,5,8,14,17,20-hexoxaheneicosane having the structural formula

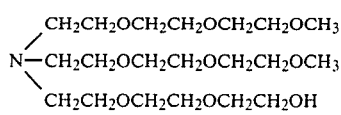

Under the conditions of Example 1, the following ingredients were reacted:

| (i) | 11-Aza-2,5,8,14,17,20-hexaoxaheneicosane | 250 g (0.80 mole) |
|---|---|---|
| (ii) | Triethylene glycol | 550 g (3.66 moles) |
| (iii) | Raney nickel, dehydrated | 50 g |

After 5 hours of reaction at 180° under a stream of hydrogen, the Raney nickel was filtered and the filtrate was heated to 300° C. under 0.1 mmHg (13.3 Pa).

325 g of the desired aminoalcohol were obtained, corresponding to a yield of 92.2%.

EXAMPLE 4

Preparation of N-(5'-hydroxy-3'-oxapentyl)-8-aza-3,6,11,14-tetraoxapentadecane having the structural formula

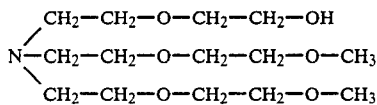

Under the conditions of Example 1, the following ingredients were reacted.

| (i) | 8-Aza-3,6,11,14-tetraoxapentadecane | 676.5 g (3 moles) |
|---|---|---|
| (ii) | Diethylene glycol | 1285 g (12 moles) |
| (iii) | Raney nickel, dehydrated | 218 g |

The mixture was maintained for 3 hours at 180°–185° C. under a 2 g/h flow of hydrogen.

After the separation of the Raney nickel, the reaction mass was distilled to recover the excess of diethylene glycol and 662 g of the desired aminoalcohol, which boiled at Bp$_1$=200° C.

The yield with respect to the secondary amine reactant was 71.5%.

EXAMPLE 5

Preparation of N-(8'-hydroxy-3',6'-dioxaoctyl)-8-aza-2,5,11,14-tetraoxapentadecane having the structural formula

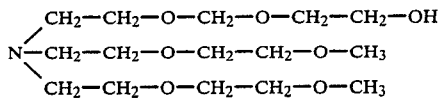

Under the conditions of Example 1, the following ingredients were reacted:

| (i) | Triethylene glycol | 890 g (6 moles) |
|---|---|---|
| (ii) | Raney Ni, dehydrated | 160 g |
| (iii) | 8-Aza-2,5,11,14-tetraoxapentadecane | 442 g (2 moles) |

After 3 hours of heating at 180° C., filtration of the Raney nickel and distillation to eliminate the triethylene glycol, 508 g of the desired aminoalcohol were recovered; same boiled at $Bp_{0.3}=193°$ C.

The yield with respect to the secondary reactant amine was 72%.

EXAMPLE 6

Complexing ability of N-(8'-hydroxy-3',6'-dioxaoctyl)-11-aza-2,5,8,14,17,20-hexaoxaheneicosane Solubilization of alkali metal thiocyanates in methylene chloride This test demonstrates the complexing ability of the compound prepared in Example 3 and was carried out as follows:

In an Erlenmeyer flask of 50 ml capacity, equipped with a reflux condenser and a magnetic agitator, 10 ml anhydrous, purified methylene chloride (devoid of stabilizer) were introduced.

Subsequently, the following materials were added:
(i) 0.001 mole of an alkali metal thiocyanate selected from among the thiocyanates of Li, Na and K;
(ii) 0.001 mole of the complexing agent to be tested.

After agitating the mixture for 10 min at ambient temperature, the same was centrifuged; the clear solution obtained in this manner was analyzed by flame spectrometry.

The test was then repeated in the absence of the complexing agent tested.

The following results were obtained:

[I] Solubilization of LiSCN
(1) Solubility measured: 690 mg/l
(2) Maximum calculated solubility: 690 mg/l
(3) Degree of solubilization: 100%
(4) Complex formed:

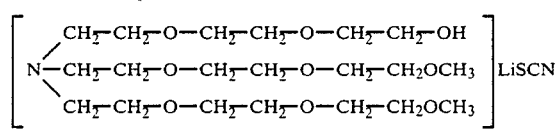

(5) Solubility measured without the complexing agent: <1 mg/l

[II] Solubilization of NaSCH
(1) Solubility measured: 2300 mg/l
(2) Maximum calculated solubility: 2300 mg/l
(3) Degree of Solubilization: 100%
(4) Complex formed:

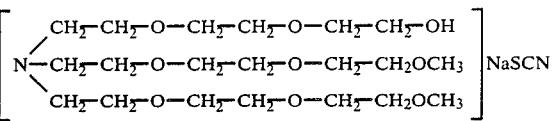

(5) Solubility measured without the complexing agent: <1 mg/l

[III] Solubilization of KSCN
(1) Solubilization measured: 3380 mg/l
(2) Maximum calculated solubility: 3910 mg/l
(3) Degree of solubilization: 86.4%
(4) Complex formed:

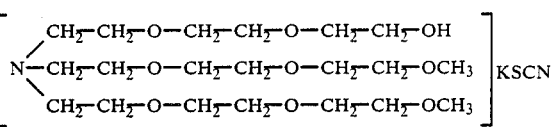

The immediately aforesaid results are summarized in the Table I which follows:

TABLE I

| Salt to be dissolved | Maximum calculated solubility | Solubility measured in the presence of the complexing agent | Solubility measured without the complexing agent |
|---|---|---|---|
| LiSCN | 690 mg/l | 690 mg/l | <1 mg/l |
| NaSCN | 2300 mg/l | 2300 mg/l | <1 mg/l |
| KSCN | 3910 mg/l | 3380 mg/l | <1 mg/l |

EXAMPLE 7

Complexing ability of N-(5'-hydroxy-3'-oxapentyl)-8-aza-3,6,11,14-tetraoxapentadecane Solubilization of alkali metal thiocyanates in methylene chloride The test described in Example 6 was repeated, but using as the complexing agent the compound of Example 4:

The results were the following:

TABLE II

| Salt to be dissolved | Maximum calculated solubility | Solubility measured in the presence of the complexing agent | Solubility measured without the complexing agent |
|---|---|---|---|
| LiSCN | 690 mg/l | 670 mg/l | <1 mg/l |
| NaSCN | 2300 mg/l | 2255 mg/l | <1 mg/l |
| KSCN | 3910 mg/l | 3640 mg/l | <1 mg/l |

(a) Degree of solubilization of: LiSCN: 97%
NaSCN: 98%
KSCN: 93%

(b) Complexes formed:

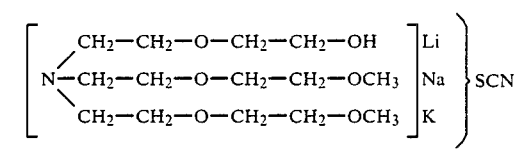

EXAMPLE 8

Complexing ability of
N-(8'-hydroxy-3',6'-dioxaoctyl)-8-aza-2,5,11,14-tetraoxapentadecane Solubilization of alkali metal thiocyanates in methylene chloride The test described in Example 6 was repeated, but using as the complexing agent to be tested the compound of Example 5:

The results were as follows:

TABLE III

| Salt to be dissolved | Maximum calculated solubility | Solubility measured in the presence of the complexing agent | Solubility measured without the complexing agent |
|---|---|---|---|
| LiSCN | 690 mg/l | 685 mg/l | <1 mg/l |
| NaSCN | 2300 mg/l | 2300 mg/l | <1 mg/l |
| KSCN | 3910 mg/l | 3640 mg/l | <1 mg/l |

(a) Degree of solubilization of:  LiSCN: 99%
 NaSCN: 100%
 KSCN: 93%

(b) Complexes formed:

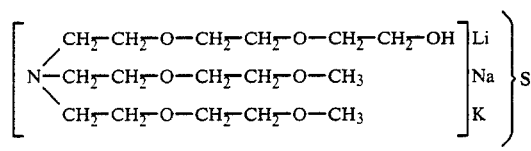

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of a polyoxaalkyl aminoalcohol having the structural formula:

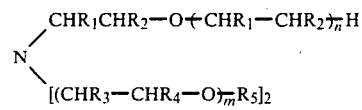

wherein $R_1$, $R_2$, $R_3$ and $R_4$, which may be identical or different, are each a hydrogen atom or an alkyl radical having from 1 to 4 carbon atoms; $R_5$ is an alkyl, or phenyl substituted alkyl radical having from 1 to 12 carbon atoms, a cycloalkyl radical having from 3 to 12 carbon atoms, a phenyl, or alkyl substituted phenyl radical with said alkyl substituent having from 1 to 12 carbon atoms; n is an integer ranging from 1 to 9; and m is an integer ranging from 1 to 10; comprising reacting a polyalkylene glycol having the structural formula:

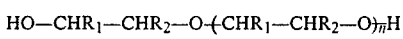

with a bis(polyoxaalkyl)amine having the structural formula:

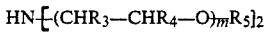

in a molar ratio of polyalkylene glycol to bis(polyoxaalkyl)amine at least 1.5 times in excess of the stoichiometric amount, at a temperature ranging from about 120° to 220° C., and in the presence of a catalytically effective amount of a hydrogenation/dehydrogenation catalyst.

2. The process as defined by claim 1, said catalyst being a nickel catalyst.

3. The process as defined by claim 2, said catalyst being Raney or Harshaw nickel, and same being present in an amount ranging from 1 to 15% by weight of the amount of the bis(polyoxaalkyl)amine reactant.

4. The process as defined by claim 3, said molar ratio excess ranging from 1.5 to 10.

5. The process as defined by claim 4, the reaction being conducted in the presence of hydrogen.

6. The process as defined by claim 5, the amount of hydrogen ranging from 1 to 10% by weight of the polyalkylene glycol reactant.

* * * * *